(12) United States Patent
Dwoskin et al.

(10) Patent No.: US 10,668,030 B2
(45) Date of Patent: Jun. 2, 2020

(54) VESICULAR MONOAMINE TRANSPORTER-2 LIGANDS AND THEIR USE IN THE TREATMENT OF PSYCHOSTIMULANT ABUSE

(71) Applicant: University of Kentucky Research Foundation, Lexington, KY (US)

(72) Inventors: Linda P. Dwoskin, Lexington, KY (US); Peter Anthony Crooks, Little Rock, AR (US); Guangrong Zheng, Little Rock, AR (US); Justin R. Nickell, Lexington, KY (US); Zheng Cao, Lexington, KY (US); Na-Ra Lee, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/493,836

(22) Filed: Apr. 21, 2017

(65) Prior Publication Data
US 2017/0304227 A1  Oct. 26, 2017

Related U.S. Application Data

(60) Provisional application No. 62/325,875, filed on Apr. 21, 2016.

(51) Int. Cl.
*A61K 31/137* (2006.01)
*A61K 31/138* (2006.01)

(52) U.S. Cl.
CPC .......... *A61K 31/137* (2013.01); *A61K 31/138* (2013.01)

(58) Field of Classification Search
None
See application file for complete search history.

(56) References Cited

U.S. PATENT DOCUMENTS

2006/0035889 A1\* 2/2006 Tedford ............... A61K 31/551
514/220

FOREIGN PATENT DOCUMENTS

WO  WO 91/09594 A1  7/1991
WO  WO 93/00313 A2  1/1993

OTHER PUBLICATIONS

German et al. "Regulation of the Dopamine and Vesicular Monoamine Transporters: Pharmacological Targets and Implications for Disease", Pharmacological Reviews, Oct. 2015; 67:1005-1024. (Year: 2015).\*
Nickell et al. "The Vesicular Monoamine Transporter-2: An Important Pharmacological Target for the Discovery of Novel Therapeutics to Treat Methamphetamine Abuse", Adv Pharmacol, 2014; 69:71-106, Abstract Only. (Year: 2014).\*
Horton et al. "GZ-293A, a Lobelane Analog, Interacts with the Vesicular Monoamine Transporter-2 to Inhibit the Effect of Methamphetamine", Journal of Neurochemistry, 2013; 127:177-186. (Year: 2013).\*
Wilmouth et al. "Oral Administration of GZ-793A, a VMAT2 Inhibitor, Decreases Methamphetamine Self-Administration in Rats", Pharmacology, Biochemistry and Behavior, 2013; 112; 29-33. (Year: 2013).\*
Nickell et al. "Preclinical Evaluation of JPC-077 as a Novel Treatment for Methamphetamine Abuse", Drug and Alcohol Dependence (Abstracts), 2014; 140:e160. (Year: 2014).\*
Cao, Zheng. "Lobelane Analogs with Various Methylene Linker Lengths and Acyclic Lobelane Analogs as Potential Pharmacotherapies to Treat Methamphetamine Abuse". (2014). Theses and Dissertations—Pharmacy. 32. Obtained from the Internet: <URL: https://uknowledge.uky.edu/pharmacy_etds/32>. (Year: 2014).\*
Patani et al. "Bioisosterism: A Rational Approach in Drug Design". Chem. Rev. 1996; 96:3147-3176. (Year: 1996).\*
Lee et al., "Enantiomers of (±)GZ-888 potently and selectively inhibit vesicular monoamine transporter-2 function and methamphetamine-stimulated locomotor activity", 2016, one page.
Teng et al., "Lobeline Diplaces [$^3$H] Dihydrotetrabenazine Binding and Releases [$^3$H] Dopamine from Rat Striatal Synaptic Vesicles: Comparison with d-Amphetamine", Journal of Neurochemistry, International Society for Neurochemistry, 1998, pp. 258-265, vol. 71, No. 1, Lippincott-Raven Publishers, Philadelphia.
Teng et al., "Lobeline and Nicotine Evoke [$^3$H]Overflow from Rat Striatal Slices Preloaded with [$^3$H]Dopamine: Differential Inhibition of Synaptosomal and Vesicular [$^3$H]Dopamine Uptakes[1]", The Journal of Pharmacology and Experimental Therapeutics, 1997, pp. 1432-1444, vol. 280, No. 3, The American Society for Pharmacology and Experimental Therapeutics.
Mark et al., "An Appetitively Conditioned Taste Elicits a Preferential Increase in Mesolimbic Dopamine Release", Pharmacology Biochemistry and Behavior, 1994, pp. 651-660, vol. 48, No. 3, Elsevier Science Ltd.
Martel et al., "Mesolimbic Dopaminergic System Activity as a Function of Food Reward: A Microdialysis Study", Pharmacology Biochemistry and Behavior, 1996, pp. 221-226, vol. 53, No. 1, Elsevier Science Inc.
Johnson et al., "Dopamine D2 receptors in addiction-like reward dysfunction and compulsive eating in obese rats", nature neuroscience, May 2010, pp. 635-641 (10 pages total), vol. 13, No. 5, Nature America, Inc.
Kelley, "Ventral striatal control of appetitive motivation: role in ingestive behavior and reward-related learning", Neuroscience and Biobehavioral Reviews, 2004, pp. 765-776, vol. 27, Elsevier.
Small et al., "Feeding-induced dopamine release in dorsal striatum correlates with meal pleasantness ratings in healthy human volunteers", NeuroImage, 2003, pp. 1709-1715, vol. 19, Academic Press.
Volkow et al., "How can drug addiction help us understand obesity?" Nature Neuroscience, May 2005, pp. 555-560, vol. 8, No. 5, Nature Publishing Group.
Wang et al., "The role of dopamine in motivation for food in humans: implications for obesity", Expert Opin. Ther. Targets, 2002, pp. 601-609, vol. 6, No. 5, Ashley Publications Ltd.
Yin et al., "Lesions of dorsolateral striatum preserve outcome expectancy but disrupt habit formation in instrumental learning", European Journal of Neuroscience, 2004, pp. 181-189, vol. 19, Federation of European Neuroscience Societies.

\* cited by examiner

*Primary Examiner* — Leslie A. Royds Draper
(74) *Attorney, Agent, or Firm* — Crowell & Moring LLP

(57) ABSTRACT

The present invention relates to methods of treatment of a disease or pathology of the central nervous system, an eating disorder, or substance use disorder, drug dependence/abuse and withdrawal therefrom comprising administering at least one N-phenylalkyl amphetamine derivative and pharmaceutical compositions comprising at least one N-phenylalkyl amphetamine derivative to an individual in need thereof.

4 Claims, No Drawings

VESICULAR MONOAMINE TRANSPORTER-2 LIGANDS AND THEIR USE IN THE TREATMENT OF PSYCHOSTIMULANT ABUSE

FIELD OF THE INVENTION

The present invention relates to methods treatment of a disease or pathology of the central nervous system, an eating disorder, or substance use disorder, drug dependence/abuse and withdrawal therefrom comprising administering N-phenylalkyl amphetamine derivatives and pharmaceutical compositions containing these compounds to an individual in need thereof.

BACKGROUND OF THE INVENTION

The action of many therapeutic neuropharmacological agents involve the modulation of dopamine (DA), norepinephrine (NE) and serotonin (5-HT) release, uptake and storage within their respective terminals in the central nervous system (CNS). Most neurotransmitters are stored in synaptic vesicles, which are prominent features of nerve terminals. Sequestration into vesicles appears to be responsible for maintaining a ready supply of neurotransmitter molecules available for neuronal exocytotic release into the synaptic cleft. Vesicles also serve the role of protecting the neurotransmitter molecules from metabolic breakdown. One transport site on the vesicle membrane is the vesicular monoamine transporter-2 (VMAT2), whose role is to transport transmitters from the cytosol into the synaptic vesicle. Once the neurotransmitter is released from the terminal into the synaptic space, it interacts with postsynaptic receptors and subsequently is taken back up into the terminal via the plasma membrane transporter (e.g., DAT and/or the serotonin transporter [SERT]). Thus, transporter proteins modify the concentration of neurotransmitters in the cytosolic and vesicular storage pools, and thereby have the ability to alter subsequent neurotransmission.

SUMMARY OF THE INVENTION

The present invention provides a compound of formula (I):

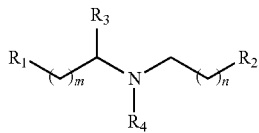

(I)

wherein
  m is an integer in the range from 1 to 3;
  n is zero or an integer in the range from 1 to 5;
  $R_1$ is an aryl group which may be substituted by one or more substituents;
  $R_2$ is an aryl group which may be substituted by one or more substituents;
  wherein substituents on $R_1$ and $R_2$ are independently selected from the group consisting of methyl; deuteromethyl ($CD_3$); tritiomethyl ($CT_3$); ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); benzyl; phenylethyl; amino; N-methylamino; N,N-dimethylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl sulfate; phenyl; methylsulfate; hydroxyl; methoxy; ethoxy; propoxy; isopropoxy; thiol; methylthio; ethylthio; propiothiol; fluoro; chloro; bromo; iodo; trifluoromethyl; vinyl; allyl; propargyl; nitro; carbamoyl; ureido; azido; isocyanate; thioisocyanate; hydroxylamino; nitroso; a saturated or unsaturated hydrocarbon ring; a nitrogen containing heterocyclic moiety; an oxygen containing heterocyclic moiety; a sulfur containing heterocyclic moiety; a selenium containing heterocyclic moiety; a mixed heterocyclic moiety containing at least two atoms selected from the group consisting of nitrogen, oxygen and sulfur; and ortho, meta or para-substituted benzene;
  $R_3$ is a methyl, ethyl, propyl, isopropyl, hydroxymethyl, 2-hydroxyethyl, 1-hyhydroxyethyl, methoxymethyl, 2-methoxyethyl, 1-methoxyethyl, aminomethyl, 2-aminoethyl, 1-aminoethyl, N-methylaminomethyl, 2-N-methylaminoethyl, 1-N-methylaminoethyl, N,N-dimethylaminomethyl, 2-N,N-dimethylaminoethyl, or 1-N,N-dimethylaminoethyl group; and
  $R_4$ is a hydrogen atom, a methyl, ethyl, propyl, or isopropyl group.

The compound of formula (I) may form pharmaceutically acceptable salts with a variety of acids.

DETAILED DESCRIPTION OF THE INVENTION

The present invention provides a compound of formula (I):

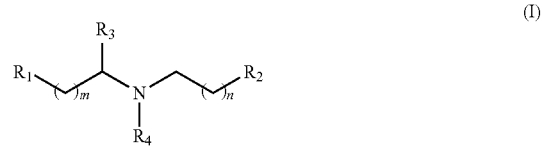

(I)

wherein
  m is an integer in the range from 1 to 3;
  n is zero or an integer from 1 to 5;
  $R_1$ and $R_2$ are each independently an aryl group,
  wherein $R_1$ and $R_2$ are each independently unsubstituted or substituted by one or more substituents selected from the group consisting of methyl; deuteromethyl ($CD_3$); tritiomethyl ($CT_3$); ethyl; propyl; isopropyl; $C_4$-$C_7$ straight chain or branched alkyl; $C_3$-$C_6$ cycloalkyl; $C_4$-$C_7$ alkenyl; benzyl; phenylethyl; amino; N-methylamino; N,N-dimethylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl sulfate; phenyl; methylsulfate; hydroxyl; methoxy; ethoxy; propoxy; isopropoxy; thiol; methylthio; ethylthio; propiothiol; fluoro; chloro; bromo; iodo; trifluoromethyl; vinyl; allyl; propargyl; nitro; carbamoyl; ureido; azido; isocyanate; thioisocyanate; hydroxylamino; nitroso; a saturated or unsaturated hydrocarbon ring; a nitrogen-containing heterocyclic moiety; an oxygen-containing heterocyclic moiety; a sulfur-containing heterocyclic moiety; a selenium-containing heterocyclic moiety; a mixed heterocyclic moiety containing at least two atoms selected from the group consisting of nitrogen, oxygen and sulfur; and ortho, meta or para-substituted benzene;

$R_3$ is methyl, ethyl, propyl, isopropyl, hydroxymethyl, 2-hydroxyethyl, 1-hyhydroxyethyl, methoxymethyl, 2-methoxyethyl, 1-methoxyethyl, aminomethyl, 2-aminoethyl, 1-aminoethyl, N-methylaminomethyl, 2-N-methylaminoethyl, 1-N-methylaminoethyl, N,N-dimethylaminomethyl, 2-N,N-dimethylaminoethyl, or 1-N,N-dimethylaminoethyl group; and $R_4$ is a hydrogen atom or a methyl, ethyl, propyl, or isopropyl group; or an enantiomer; racemate; or pharmaceutically acceptable salt thereof.

A further embodiment of the invention is a compound of formula (I), wherein: m is 1 or 2; and n is an integer from 1 to 5; or an enantiomer; racemate; or pharmaceutically acceptable salt thereof.

An further embodiment of the invention is a compound of formula (I), wherein: m is 1 or 2; and n is an integer from 1 to 5; $R_3$ is methyl, ethyl, propyl, or isopropyl; and $R_4$ is a hydrogen atom or a methyl, ethyl, propyl, or isopropyl group; or an enantiomer; racemate; or pharmaceutically acceptable salt thereof.

A further embodiment of the invention is a compound of formula (I), wherein: m is 1 or 2; and n is an integer from 1 to 5; wherein $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 1; n is 1; $R_1$ and $R_2$ are each independently a phenyl group, wherein $R_1$ and $R_2$ are each independently unsubstituted or substituted by one or more substituents selected from the group consisting of benzyl; amino; hydroxyl; methoxy; fluoro; bromo; and nitroso; $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 1; n is 2; $R_1$ and $R_2$ are each independently a phenyl group, wherein $R_1$ and $R_2$ are each independently unsubstituted or substituted by one or more substituents selected from the group consisting of benzyl; amino; hydroxyl; methoxy; fluoro; bromo; and nitroso; $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 2; n is 1; $R_1$ and $R_2$ are each independently a phenyl group, wherein $R_1$ and $R_2$ are each independently unsubstituted or substituted by one or more substituents selected from the group consisting of methoxy and bromo; $R_3$ is methyl; and $R_4$ is a hydrogen atom; or an enantiomer; racemate; or pharmaceutically acceptable salt thereof.

Yet another embodiment of the invention is a compound of formula (I), wherein m is 2; n is 2; $R_1$ and $R_2$ are each independently a phenyl group, wherein $R_1$ and $R_2$ are each independently unsubstituted or substituted by one or more methoxy groups; $R_3$ is methyl; and $R_4$ is a hydrogen atom or a methyl group; or an enantiomer; racemate; or pharmaceutically acceptable salt thereof.

Yet another embodiment of the invention is a compound of formula (I), wherein m is 1; n is an integer from 3 to 5; $R_1$ and $R_2$ are each independently a phenyl group, wherein $R_1$ and $R_2$ are each independently unsubstituted or substituted by one or more substituents selected from the group consisting of methoxy and bromo; $R_3$ is methyl; and $R_4$ is a hydrogen atom; or an enantiomer; racemate; or pharmaceutically acceptable salt thereof.

Yet another embodiment of the invention is a compound of formula (I), wherein m is 1; n is 2; $R_1$ is an unsubstituted phenyl group; $R_2$ is a phenyl group substituted with a methoxy group; $R_3$ is methyl; and $R_4$ is a hydrogen atom; or an enantiomer; racemate; or pharmaceutically acceptable salt thereof.

Compounds of formula (I) include the following compounds:

1. m=1, n=1, $R_1$=Ph, $R_2$=Ph, $R_3$=Me, $R_4$=H
2. m=1, n=1, $R_1$=Ph, $R_2$=Ph, $R_3$=Me, $R_4$=$CH_3$
3. m=1, n=1, $R_1$=4-BrPh, $R_2$=Ph, $R_3$=Me, $R_4$=H
4. m=1, n=2, $R_1$=Ph, $R_2$=Ph, $R_3$=Me, $R_4$=H
5. R—, m=1, n=2, $R_1$=Ph, $R_2$=Ph, $R_3$=Me, $R_4$=H
6. S—, m=1, n=2, $R_1$=Ph, $R_2$=Ph, $R_3$=Me, $R_4$=H
7. m=1, n=2, $R_1$=Ph, $R_2$=Ph, $R_3$=Me, $R_4$=$CH_3$
8. m=1, n=2, $R_1$=Ph, $R_2$=4-MeOPh, $R_3$=Me, $R_4$=H
9. R—, m=1, n=2, $R_1$=Ph, $R_2$=4-MeOPh, $R_3$=Me, $R_4$=H
10. S—, m=1, n=2, $R_1$=Ph, $R_2$=4-MeOPh, $R_3$=Me, $R_4$=H
11. m=1, n=2, $R_1$=4-BrPh, $R_2$=Ph, $R_3$=Me, $R_4$=H
12. R—, m=1, n=2, $R_1$=4-BrPh, $R_2$=Ph, $R_3$=Me, $R_4$=H
13. S—, m=1, n=2, $R_1$=4-BrPh, $R_2$=Ph, $R_3$=Me, $R_4$=H
14. m=1, n=3, $R_1$=4-BrPh, $R_2$=Ph, $R_3$=Me, $R_4$=H
15. m=1, n=3, $R_1$=Ph, $R_2$=Ph, $R_3$=Me, $R_4$=H
16. m=1, n=2, $R_1$=4-BrPh, $R_2$=4-MeOPh, $R_3$=Me, $R_4$=H
17. m=1, n=4, $R_1$=Ph, $R_2$=Ph, $R_3$=Me, $R_4$=H
18. m=1, n=5, $R_1$=Ph, $R_2$=Ph, $R_3$=Me, $R_4$=H
19. m=1 n=1, $R_1$=Ph, $R_2$=PhO, $R_3$=Me, $R_4$=H
20. m=1, n=1, $R_1$=4-BrPh, $R_2$=PhO, $R_3$=Me, $R_4$=H
21. m=1, n=1, $R_1$=Ph, $R_2$=4-OHPh, $R_3$=Me, $R_4$=H
22. m=1, n=1, $R_1$=Ph, $R_2$=3,4-diBnOPh, $R_3$=Me, $R_4$=H
23. m=1, n=1, $R_1$=Ph, $R_2$=3,4-diOHPh, $R_3$=Me, $R_4$=H
24. m=1, n=1, $R_1$=4-MeOPh, $R_2$=Ph, $R_3$=Me, $R_4$=H
25. m=1, n=1, $R_1$=4-MeOPh, $R_2$=Ph, $R_3$=Me, $R_4$=$CH_3$
26. m=1, n=2, $R_1$=4-MeOPh, $R_2$=Ph, $R_3$=Me, $R_4$=H
27. R—, m=1, n=2, $R_1$=4-MeOPh, $R_2$=Ph, $R_3$=Me, $R_4$=H
28. S—, m=1, n=2, $R_1$=4-MeOPh, $R_2$=Ph, $R_3$=Me, $R_4$=H
29. m=1, n=2, $R_1$=4-MeOPh, $R_2$=4-MeOPh, $R_3$=Me, $R_4$=H
30. m=1, n=2, $R_1$=4-MeOPh, $R_2$=Ph, $R_3$=Me, $R_4$=$CH_3$
31. m=2, n=1, $R_1$=4-MeOPh, $R_2$=Ph, $R_3$=Me, $R_4$=H
32. m=2, n=2, $R_1$=4-MeOPh, $R_2$=Ph, $R_3$=Me, $R_4$=H
33. m=2, n=1, $R_1$=4-MeOPh, $R_2$=4-MeOPh, $R_3$=Me, $R_4$=H
34. m=2, n=1, $R_1$=4-MeOPh, $R_2$=4-BrPh, $R_3$=Me, $R_4$=H
35. m=1, n=1, $R_1$=4-OHPh, $R_2$=Ph, $R_3$=Me, $R_4$=H
36. m=1, n=2, $R_1$=4-OHPh, $R_2$=4-MeOPh, $R_3$=Me, $R_4$=H
37. m=1, n=2, $R_1$=4-OHPh, $R_2$=Ph, $R_3$=Me, $R_4$=H
38. m=1, n=1, $R_1$=4-FPh, $R_2$=Ph, $R_3$=Me, $R_4$=H
39. m=1, n=2, $R_1$=4-FPh, $R_2$=Ph, $R_3$=Me, $R_4$=H
40. m=1, n=2, $R_1$=4-FPh, $R_2$=4-MeOPh, $R_3$=Me, $R_4$=H
41. m=1, n=1, $R_1$=4-$NO_2$Ph, $R_2$=Ph, $R_3$=Me, $R_4$=H
42. m=1, n=2, $R_1$=4-$NO_2$Ph, $R_2$=Ph, $R_3$=Me, $R_4$=H
43. m=1, n=2, $R_1$=4-$NO_2$Ph, $R_2$=4-MeOPh, $R_3$=Me, $R_4$=H
44. m=1, n=1, $R_1$=4-$NH_2$Ph, $R_2$=Ph, $R_3$=Me, $R_4$=H
45. m=1, n=2, $R_1$=4-$NH_2$Ph, $R_2$=Ph, $R_3$=Me, $R_4$=H
46. m=1, n=2, $R_1$=3,4-diMeOPh, $R_2$=Ph, $R_3$=Me, $R_4$=H
47. m=1, n=3, $R_1$=3,4-diMeOPh, $R_2$=Ph, $R_3$=Me, $R_4$=H
48. m=2, n=1, $R_1$=Ph, $R_2$=Ph, $R_3$=Me, $R_4$=H
49. m=2, n=1, $R_1$=Ph, $R_2$=Ph, $R_3$=Me, $R_4$=H
50. m=2, n=2, $R_1$=Ph, $R_2$=Ph, $R_3$=Me, $R_4$=H
51. m=2, n=2, $R_1$=Ph, $R_2$=Ph, $R_3$=Me, $R_4$=$CH_3$
52. m=2, n=2, $R_1$=Ph, $R_2$=4-MeOPh, $R_3$=Me, $R_4$=H
53. m=2, n=2, $R_1$=4-MeOPh, $R_2$=4-MeOPh, $R_3$=Me, $R_4$=H.

Definitions

The term "aryl" refers to aromatic groups having 6 to 24 carbon atoms, and "substituted aryl" refers to aryl groups further bearing one or more substituents.

The term "alkyl" refers to straight or branched chain alkyl radicals having 1 to 19 carbon atoms, and "substituted alkyl" refers to alkyl radicals further bearing one or more substituents.

The term "lower alkyl" refers to straight or branched chain alkyl radicals having in the range of 1 to 4 carbon atoms.

The term "cycloalkyl" refers to cyclic ring-containing moieties containing 3 to 8 carbon atoms, and "substituted cycloalkyl" refers to cycloalkyl moieties further bearing one or more substituents.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents.

Pharmaceutically acceptable salts include $Cl^-$, $Br^-$, $I^-$, $NO_2^-$, $HSO_4^-$, $SO_4^-$, $HPO_4^-$, $PO_4^{2-}$, ethanesulfonate, trifluoromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar acid addition salts. The above salt forms may be in some cases hydrates or solvates with alcohols and other solvents.

Pharmaceutical Compositions

Also disclosed herein are pharmaceutical compositions comprising a compound of formula (I) and pharmaceutically acceptable excipients. For example, the pharmaceutical composition may include a pharmaceutically acceptable additive, such as a stabilizer, buffer, salt, preservative, filler, flavor enhancer and the like, as known to those skilled in the art. Representative buffers include phosphates, carbonates, and citrates. Exemplary preservatives include EDTA, EGTA, BHA, and BHT.

The pharmaceutical composition disclosed herein may be administered by inhalation (i.e., intranasally as an aerosol or nasal formulation); topically (i.e., in the form of an ointment, cream or lotion); orally (i.e., in solid or liquid form (tablet, capsule, gel cap, time release capsule, powder, solution, or suspension in aqueous or non-aqueous liquid); intravenously as an infusion or injection (i.e., as a solution, suspension or emulsion in a pharmaceutically acceptable carrier); or subcutaneously as an infusion or injection (i.e., as a solution, suspension or emulsion in a pharmaceutically acceptable carrier) or as a depot formulation; transdermally (e.g., via a transdermal patch), or rectally (e.g., as a suppository).

There is no limitation in the route of administration or dosage form, and the composition may be administered in accordance with specific form of the preparation, age, sex and the other conditions of a patient, severity of disease, etc. For example, in the case of tablet, pill, solution, suspension, emulsion, granule and capsule, the composition is orally administered. In the case of injection, the composition is intravenously administered alone or in a mixture with conventional replacement fluid such as glucose and amino acids, and if necessary, and the preparation alone may be also administered intramuscularly, intracutaneously, subcutaneously or interperitoneally.

The compounds disclosed herein can be administered alone, combined with a pharmaceutically acceptable excipient, or co-administered with a second drug. Co-administration may provide a similar or synergistic effect. A compound of formula (I) or a pharmaceutically acceptable salt thereof can be administered subcutaneously, intramuscularly, intravenously, transdermally, orally, intranasally, intrapulmonary, or rectally.

The dose of the pharmaceutical composition of the present invention is appropriately selected in accordance with dosage regimen, age, sex and the other conditions of a patient. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like.

The pharmaceutical composition may comprise a compound of formula (I), or an enantiomer or racemate thereof, or pharmaceutically acceptable salt thereof, and a pharmaceutically acceptable additive or a pharmaceutically acceptable excipient.

Treatment of Drug Abuse

VMAT2 is considered as a valid target for the development of treatments for the abuse of drugs, including, for example, methamphetamine (METH), amphetamine, cocaine, methylphenidate, and opiate abuse. For example, METH decreases vesicular DA sequestration by inhibiting vesicular uptake through VMAT2 ($IC_{50}$=14.9 μM) and by diffusing across the vesicular membranes to decrease the pH gradient, resulting in the loss of free energy needed for monoamine transport.

Lobelane competitively inhibits [$^3$H]DA uptake into rat brain vesicles via interaction with VMAT2 ($K_i$=45 nM), decreases METH-evoked DA overflow from rat striatal slices, and decreases METH self-administration, but does not act as a psychostimulant, suggesting that it has potential as a novel treatment for METH abuse. Nor-Lobelane ($K_i$=44 nM) is equipotent with lobelane at VMAT2 in inhibiting [$^3$H]DA uptake.

METH can be considered as a structural fragment of lobelane/nor-lobelane, and introducing bulky substituents onto the N-atom of METH afforded compounds with increased inhibitory potency at VMAT2, reduced the psychostimulant effects of METH, diminishing its abuse potential. Importantly, these new analogs did not increase locomotor activity in rats, indicating they do not act as psychostimulants. Lee, N.-R. et al., *Drug and Alcohol Dependence*, "Enantiomers of (±)GZ-888 potently and selectively inhibit vesicular monoamine transporter-2 function and methamphetamine-stimulated locomotor activity," (2016).

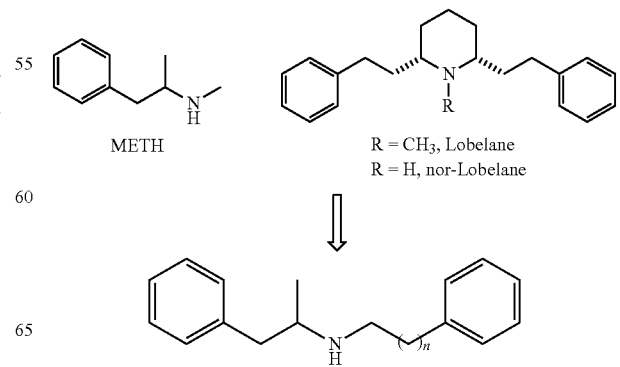

Treatment of a Disease or Pathology of the Central Nervous System or an Eating Disorder Modulation of VMAT2 has potential as a therapeutic for central nervous system diseases or pathologies. Thus, VMAT2 is a target for the development of treatments for a disease or pathology of the central nervous system, including, for example, cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit hyperactivity disorder, hyperkinetic syndrome, chronic nervous exhaustion, narcolepsy, pain, motion sickness, and/or depression.

VMAT2 is also a target for the development of treatments for eating disorders, including, for example, obesity. Compulsive eating is linked to addiction-like neuroadaptive responses in brain reward circuits. Johnson, P. M. et al., "Dopamine D2 receptors in addiction-like reward dysfunction and compulsive eating in obese rats," Nature Neuroscience, 2010, 13, 635-641. Modulation of VMAT2 may lead to reduced reward responses, diminishing overeating.

A more preferred embodiment of the invention is a compound of formula (I), wherein the compound is 3-(4-methoxyphenyl)-N-(1-phenylpropan-2-yl)propan-1-amine or an enantiomer; racemate; or pharmaceutically acceptable salt thereof.

An even more preferred embodiment of the invention is a compound of formula (I), wherein the compound is (S)-3-(4-methoxyphenyl)-N-(1-phenylpropan-2-yl)propan-1-amine hydrochloride.

A more preferred embodiment of the invention is a pharmaceutical composition comprising 3-(4-methoxyphenyl)-N-(1-phenylpropan-2-yl)propan-1-amine or an enantiomer; racemate; or pharmaceutically acceptable salt thereof and a pharmaceutically acceptable additive or a pharmaceutically acceptable excipient. An even more preferred embodiment of the invention is a pharmaceutical composition comprising (S)-3-(4-methoxyphenyl)-N-(1-phenylpropan-2-yl)propan-1-amine hydrochloride and a pharmaceutically acceptable additive or a pharmaceutically acceptable excipient.

Another preferred embodiment of the invention is a method of treating a disease or pathology of the central nervous system or an eating disorder in an individual in need thereof, wherein the method comprises the step of administering to the individual a compound of formula (I) or a pharmaceutically acceptable salt thereof.

The compounds of the present invention may be used in a method of treating a disease or pathology of the central nervous system, wherein the disease may be cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit hyperactivity disorder, hyperkinetic syndrome, chronic nervous exhaustion, narcolepsy, pain, motion sickness, and/or depression.

The compounds of the present invention may also be used in a method of treating an eating disorder. The eating disorder may be obesity.

The compounds of the present invention may be used in a method of treating substance use disorder, drug dependence/abuse or withdrawal from drug dependence/abuse in an individual in need thereof. Substance use disorder and drug dependence/abuse includes dependence/abuse of psychostimulants or drugs that release dopamine. For example, the drug which the individual is using and/or dependent upon may be amphetamine, methamphetamine, and other drugs that release dopamine.

EXAMPLES

A series of VMAT2 inhibitors were synthesized and evaluated for their activity at VMAT2, dopamine transporters (DAT), and serotonin transporters (SERT) using rat striatum, hERG channels expressed by HEK-293 cells, and for their effect on METH-stimulated locomotor activity in rats. Compounds of the invention exhibited affinity at VMAT2 as well as selectivity at VMAT2 over hERG, DAT, and SERT. Further, a significant reduction of METH-stimulated locomotor activity was observed after administration of the compounds.

Example 1

Synthesis of compound 10. (S)-3-(4-methoxyphenyl)-N-(1-phenylpropan-2-yl)propan-1-amine To a solution of phenyllithium (50 mL, 1.8 M in dibutyl ether) in THF (50 mL) was added (R)-propylene oxide (5 g) dropwise at −78° C. The resulting mixture was stirred at the same temperature for 1 hr before warmed to room temperature. After stirred at room temperature overnight, the reaction was quenched by adding saturated $NH_4Cl$ aqueous solution. The aqueous phase was extracted with ethyl acetate (3×50 mL) and the combined organic layers were washed with brine (100 mL), dried over anhydrous $Na_2SO_4$, filtered and concentrated under reduced pressure. The crude product was chromatographed on silica (hexanes/ethyl acetate 10:1 to 3:1) to afford (R)-1-phenylpropan-2-ol (10.4 g) as a colorless oil.

To a solution of (R)-1-phenylpropan-2-ol (4.16 g, 30.50 mmol) and triethylamine (7.72 g, 10.64 mL, 76.27 mmol) in dichloromethane (100 mL) was added methanesulfonyl chloride (4.54 gm, 3.07 mL, 39.65 mmol) dropwise at 0° C. The resulting mixture was stirred at 0° C. for 15 min. Dichloromethane (100 mL) was added to the mixture and then washed with water (2×150 mL). The organic layer was dried over anhydrous $Na_2SO_4$, filtered and concentrated under reduced pressure. The resulting light yellow oil was mixed with sodium azide (5.95 g, 91.5 mmol) in DIME (40 mL) and heated at 55° C. for 3 hrs. The reaction mixture was diluted with diethyl ether (150 mL) and washed with water (2×100 mL) and brine (100 mL). The organic layer was dried over anhydrous $Na_2SO_4$, filtered and concentrated under reduced pressure. The crude product was chromatographed on silica (hexanes/ethyl acetate 50:1 to 20:1) to afford (S)-(2-azidopropyl)benzene (4.38 g) as a colorless oil.

To a solution of (S)-(2-azidopropyl)benzene (4.0 g, 24.81 mmol) in THF (90 mL) and water (10 mL) was added triphenylphosphine (9.11 g, 34.74 mmol) at room temperature. The resulting mixture was stirred for 18 hrs and water (50 mL) was added. The resulting mixture was treated with HCl (1.0 M) to pH~1 and the aqueous phase was extracted with diethyl ether (3×100 mL) and dichloromethane (2×100 mL). NaOH (15%) was added dropwise to the aqueous phase to adjust the pH to about 11 and extracted with dichloromethane (5×60 mL). The combined organic layers were dried over anhydrous $Na_2SO_4$, filtered and concentrated under reduced pressure to afford (S)-1-phenylpropan-2-amine as a colorless oil. The crude amino product (3.03 g, 22.41 mmol) was mixed with 3-(4-methoxyphenyl)propanoic acid (4.44 g, 24.65 mmol), and HOBt (3.63 g, 26.89 mmol) in dichloromethane (60 mL) at room temperature. Triethylamine (5.67 g, 56.03 mmol) was added followed by EDCI (5.15 g, 26.89 mmol). The resulting mixture was stirred overnight. The reaction mixture was diluted with dichloromethane (100 mL) and washed with water (3×50 mL), and brine (50 mL). The organic layer was dried over anhydrous $Na_2SO_4$, filtered and concentrated under reduced pressure. The crude product was chromatographed on silica (dichloromethane/ethyl acetate 10:1) to afford (S)-3-(4-methoxyphenyl)-N-(1-phenylpropan-2-yl)propanamide (6.18 g) as a white solid. (S)-3-(4-Methoxyphenyl)-N-(1-phenylpropan-2-yl)propanamide (5.0 g, 16.81 mmol) in THF was cooled to 0° C. LAH (60 mL, 1.0 M in THF) was added dropwise and the resulted reaction mixture was heated at reflux for 6 hrs. After cooled to 0° C., water (2.28 mL) was carefully added, followed by NaOH (15%, 2.28 mL) and water (6.84 mL). The resulted mixture was warmed to room temperature and stirred for 2 hrs. Filtered over celite and washed with ethyl acetate. The filtrate was concentrated under reduced pressure and the crude product was chromatographed on silica (dichloromethane/methanol 30:1 to 10:1) to afford compound 10 (4.3 g) as a white solid.

Example 2

[$^3$H]Dihydrotetrabenazine ([$^3$H]DTBZ) Binding Assay, Vesicular Preparation

Synaptic vesicles were prepared from rat brain using a modification of a previously described procedure (Teng et al., 1998). Briefly, fresh whole brain (excluding cerebellum) was homogenized using a Teflon pestle (clearance 0.003 inches) with 7 vertical strokes at 800 rpm in 20 vol of ice-cold 0.32 M sucrose and centrifuged at 1000 g for 12 min at 4° C. The resulting supernatant ($S_1$) was then centrifuged at 22,000 g for 10 min at 4° C. The synaptosomal pellets ($P_2$) were homogenized in 18 mL of ice-cold Milli-Q water and exposed for 5 min for lysing synaptosomes. Osmolarity was restored by addition of 2 mL of 25 mM HEPES with 100 mM dipotassium tartrate (pH 7.5). Samples were centrifuged at 20,000 g for 20 min at 4° C. to remove lysed synaptosomal membranes. $MgSO_4$ (1 mM) was added to the supernatant ($S_3$), and was centrifuged at 100,000 g for 45 min at 4° C. The final vesicular pellets ($P_4$) were resuspended in ice-cold assay buffer (see below) providing~15 μg protein/100 μL, determined by the method of Bradford (1976) using bovine serum albumin as a the standard. Aliquot parts (100 μL) of suspension of vesicle membrane protein were incubated in assay buffer (25 mM HEPES, 100 mM dipotassium tartrate, 5 mM $MgSO_4$, 0.1 mM EDTA and 0.05 mM EGTA, pH 7.5, at 25° C.) in the presence of 3 nM [$^3$H]DTBZ and at least 7 concentrations (1 nM-1 mM) of compound for 1 hr at room temperature. Nonspecific binding was determined in the presence of 20 μM tetrabenazine, a standard compound. Assays were performed in duplicate using a 96-well plate format. Reactions were terminated by filtration of samples on a Unifilter-96 GF/B filter plates (presoaked in 0.5% polyethylenimine), using a FilterMate harvester (Packard BioScience Co., Meriden, Conn.). After washing 5 times with 350 μL of the ice-cold wash buffer (25 mM HEPES, 100 mM dipotassium tartrate, 5 mM $MgSO_4$ and 10 mM NaCl, pH 7.5), filter plates were dried, sealed and each well filled with 40 μL Packard's MicroScint 20 cocktail. Bound [$^3$H]DTBZ was measured using a Packard TopCount NXT scintillation counter with a Packard Windows NT based operating system.

Example 3

[$^3$H]Dopamine ([$^3$H]DA) Uptake Assay, Vesicular Preparation

Inhibition of [$^3$H]DA uptake was conducted using isolated synaptic vesicle preparations (Teng et al., 1997). Briefly, rat striata were homogenized with 10 up-and-down strokes of a Teflon pestle homogenizer (clearance~0.003") in 14 ml of 0.32 M sucrose solution. Homogenates were centrifuged (2,000 g for 10 min at 4° C.), and then the supernatants were centrifuged (10,000 g for 30 min at 4° C.). Pellets were resuspended in 2 ml of 0.32 M sucrose solution and subjected to osmotic shock by adding 7 ml of ice-cold MilliQ water to the preparation. After 1 min, osmolarity was restored by adding 900 μl of 0.25 M HEPES buffer and 900 μl of 1.0 M potassium tartrate solution. Samples were centrifuged (20,000 g for 20 min at 4° C.), and the supernatants were centrifuged (55,000 g for 1 hr at 4° C.), followed by addition of 100 μl of 10 mM $MgSO_4$, 100 μl of 0.25 M HEPES and 100 μl of 1.0 M potassium tartrate solution prior to the final centrifugation (100,000 g for 45 min at 4° C.). Final pellets were resuspended in 2.4 ml of assay buffer (25 mM HEPES, 100 mM potassium tartrate, 50 μM EGTA, 100 μM EDTA, 1.7 mM ascorbic acid, 2 mM ATP-$Mg^{2+}$, pH 7.4). Aliquots of the vesicular suspension (100 μl) were added to tubes containing assay buffer, various concentrations of compound (0.1 nM-10 mM) and 0.1 μM [$^3$H]DA in a final volume of 500 μl, and incubated at 37° C. for 8 min. Nonspecific uptake was determined in the presence of the standard compound, Ro4-1284 (10 μM). Reactions were terminated by filtration, and radioactivity retained by the filters was determined by liquid scintillation spectrometry (Tri-Carb 2100TR liquid scintillation analyzer; PerkinElmer Life and Analytical Sciences, Boston, Mass.).

Example 4

[$^3$H]Dofetilide Binding Assay, HEK-293 Cell Membrane Preparation

[$^3$H]Dofetilide binding assays were conducted using commercially available HEK-293 cell membranes which stably express the hERG channel. Membranes were suspended in assay buffer (50 mM Tris, 10 mM KCl, 1 mM $MgCl_2$, pH 7.4) prior to the experiment. Assays were performed in duplicate in a total volume of 250 μL. Aliquots of the HEK-293 cell membrane suspension which contained 5 μg membrane protein were added to tubes containing assay buffer, 5 nM [$^3$H]dofetilide and a range of concentrations of analog (10 nM-100 μM). Nonspecific binding was determined in the presence of amitriptyline (1 mM). Samples were incubated for 1 hr. at 24° C., followed by rapid filtration. Radioactivity retained by the filters was determined by liquid scintillation spectrometry as described above for the [$^3$H]DA uptake assay. The affinity for the [$^3$H]dofetilide binding site on the hERG channel expressed in the HEK-293 cellular membrane was determined from the analog concentration response curves.

Example 5

[$^3$H]DA and [$^3$H]5-HT Uptake Assay, Synaptosomal Preparation

[$^3$H]DA and [$^3$H]5-HT uptake into striatal synaptosomes was determined to evaluate compound inhibition of the dopamine transporter (DAT) and the serotonin transporter (SERT), respectively. Striata from individual rats were homogenized in ice-cold sucrose solution containing 5 mM $NaHCO_3$ (pH 7.4), with 16 up-and-down strokes of a Teflon pestle homogenizer (clearance≈0.003"). Homogenates were centrifuged at 2000 g for 10 min at 4° C., and resulting supernatants were centrifuged at 20,000 g for 17 min at 4° C. Pellets were resuspended in 2.4 mL (for DAT assays) or 1.5 mL (for SERT assays) of assay buffer (125 mM NaCl, 5 mM KCl, 1.5 mM $MgSO_4$, 1.25 mM $CaCl_2$, 1.5 mM $KH_2PO_4$, 10 mM alpha-D-glucose, 25 mM HEPES, 0.1 mM EDTA, 0.1 mM pargyline, 0.1 mM ascorbic acid, saturated with 95% $O_2$/5% $CO_2$, pH 7.4). Assays were performed in duplicate in a total volume of 500 μL (for DAT assays) or 250 μL (for SERT assays). Aliquots of the synaptosomal suspension (25 μL for DAT, 50 μL for SERT) were added to tubes containing assay buffer and various concentrations of analog (1 nM-100 μM), and incubated at 34° C. for 5 min. Nonspecific uptake was determined in the presence of nomifensine (10 μM) for DAT assays or fluoxetine (10 μM) for SERT assays. GBR-12935 (100 nM) was included in the assay buffer for the SERT assay to maximally inhibit [$^3$H] 5-HT uptake through DAT and isolate uptake to SERT. Samples were placed on ice, and 50 μL of 0.1 μM [$^3$H]DA (for DAT assays) or 25 μL of 0.1 μM [$^3$H]5-HT (for SERT assays) was added to each tube, and incubated for 10 min at 34° C. Reactions were terminated by addition of 3 mL of ice-cold assay buffer and subsequent filtration and radioactivity retained by the filters was determined by liquid scintillation spectrometry (Tri-Carb 2100TR liquid scintillation analyzer; PerkinElmer Life and Analytical Sciences, Boston, Mass.).

Exemplary compounds 1-53 were tested in [$^3$H]dihydrotetrabenazine ([$^3$H]DTBZ) binding assay according to Example 2 and the [$^3$H]dopamine ([$^3$H]DA) uptake assay according to Example 3. The results of these assays are set forth in Table 1.

TABLE 1

| Compound | Structure | [$^3$H]DTBZ binding (Ki) VMAT2 (μM) | [$^3$H]DA Uptake (Ki) VMAT2 (μM) |
|---|---|---|---|
| 1 | 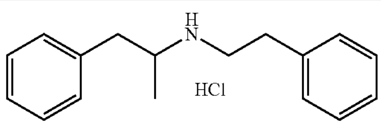 [SMILES: CC(Cc1ccccc1)NCCc1ccccc1 ; Cl] | 7.70 ± 1.25 | 0.063 ± 0.005 |
| 2 | 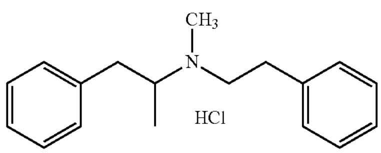 [SMILES: CC(Cc1ccccc1)N(C)CCc1ccccc1 ; Cl] | 7.53 ± 2.16 | 0.51 ± 0.10 |
| 3 | 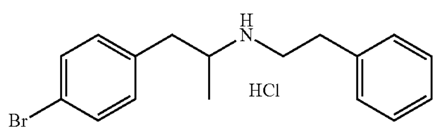 [SMILES: CC(Cc1ccc(Br)cc1)NCCc1ccccc1 ; Cl] | 1.23 ± 0.13 | 0.033 ± 0.007 |
| 4 | 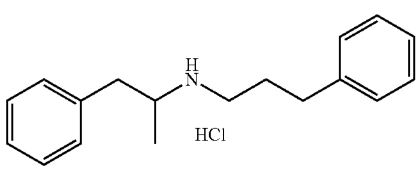 [SMILES: CC(Cc1ccccc1)NCCCc1ccccc1 ; Cl] | 1.13 ± 0.31 | 0.007 ± 0.002 |
| 5 | 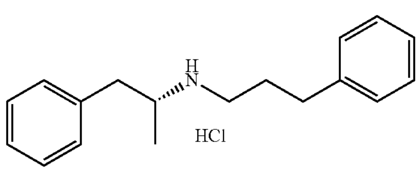 [SMILES: C[C@H](Cc1ccccc1)NCCCc1ccccc1 ; Cl] | 0.91 ± 0.59 | 0.006 ± 0.001 |
| 6 | 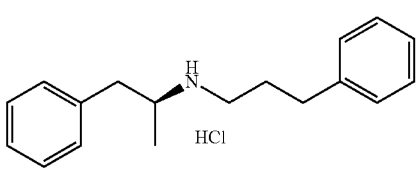 [SMILES: C[C@@H](Cc1ccccc1)NCCCc1ccccc1 ; Cl] | 0.75 ± 0.14 | 0.065 ± 0.004 |
| 7 | 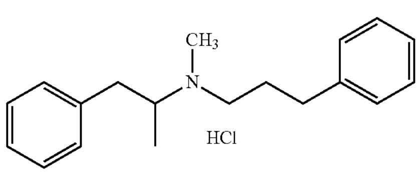 [SMILES: CC(Cc1ccccc1)N(C)CCCc1ccccc1 ; Cl] | 1.56 ± 0.47 | 0.096 ± 0.010 |

TABLE 1-continued

| Compound | Structure | [³H]DTBZ binding (Ki) VMAT2 (µM) | [³H]DA Uptake (Ki) VMAT2 (µM) |
|---|---|---|---|
| 8 | 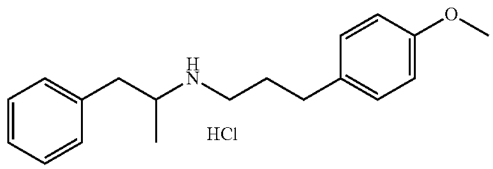 [SMILES: COc1ccc(CCCNC(C)Cc2ccccc2)cc1 ; Cl] | 2.2 ± 0.11 | 0.014 ± 0.003 |
| 9 | 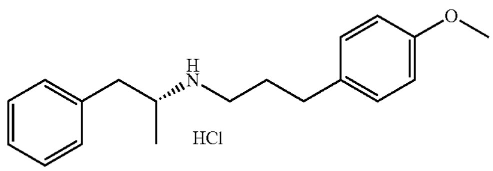 [SMILES: COc1ccc(CCCN[C@H](C)Cc2ccccc2)cc1 ; Cl] | — | 0.0087 ± 0.0065 |
| 10 | 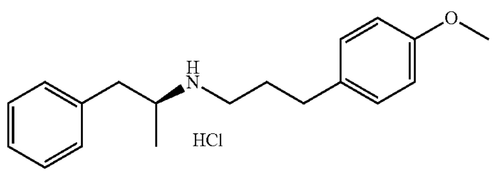 [SMILES: COc1ccc(CCCN[C@@H](C)Cc2ccccc2)cc1 ; Cl] | — | 0.026 ± 0.0036 |
| 11 | 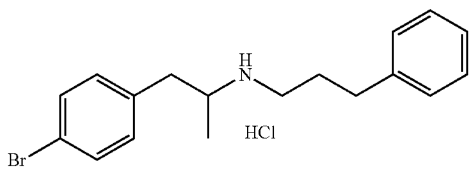 [SMILES: CC(Cc1ccc(Br)cc1)NCCCc1ccccc1 ; Cl] | 0.70 ± 0.063 | 0.008 ± 0.001 |
| 12 | 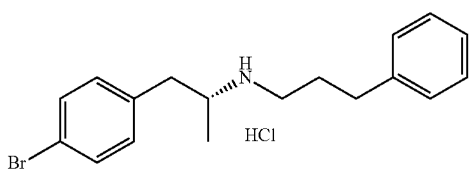 [SMILES: C[C@H](Cc1ccc(Br)cc1)NCCCc1ccccc1 ; Cl] | — | 0.006 ± 0.001 |
| 13 | 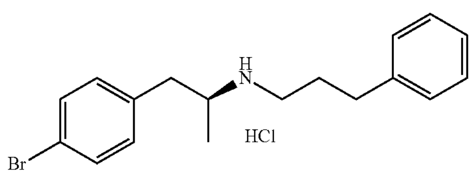 [SMILES: C[C@@H](Cc1ccc(Br)cc1)NCCCc1ccccc1 ; Cl] | — | 0.032 ± 0.004 |
| 14 | 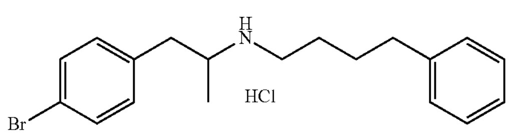 [SMILES: CC(Cc1ccc(Br)cc1)NCCCCc1ccccc1 ; Cl] | 0.081 ± 0.016 | 0.003 ± 0.0003 |
| 15 | 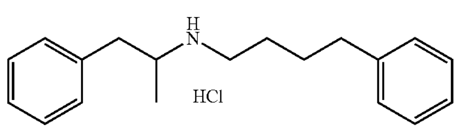 [SMILES: CC(Cc1ccccc1)NCCCCc1ccccc1 ; Cl] | 0.19 ± 0.020 | 0.003 ± 0.002 |
| 16 | 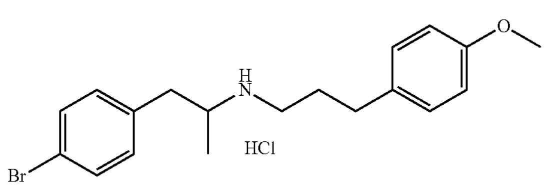 [SMILES: COc1ccc(CCCNC(C)Cc2ccc(Br)cc2)cc1 ; Cl] | 0.46 ± 0.08 | 0.012 ± 0.003 |

TABLE 1-continued
| Compound | Structure | [³H]DTBZ binding (Ki) VMAT2 (μM) | [³H]DA Uptake (Ki) VMAT2 (μM) |
|---|---|---|---|
| 17 | 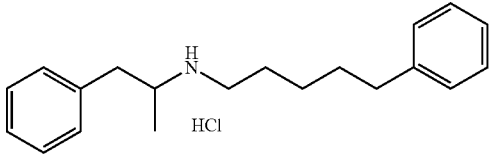 [SMILES: CC(Cc1ccccc1)NCCCCCc1ccccc1 ; Cl] | 0.63 | 0.014 ± 0.001 |
| 18 | 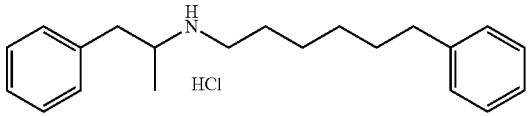 [SMILES: CC(Cc1ccccc1)NCCCCCCc1ccccc1 ; Cl] | 0.91 ± 0.59 | 0.009 ± 0.002 |
| 19 | 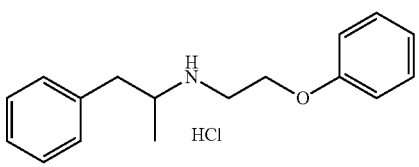 [SMILES: CC(Cc1ccccc1)NCCOc1ccccc1 ; Cl] | 4.1 ± 0.3 | 0.059 ± 0.007 |
| 20 | 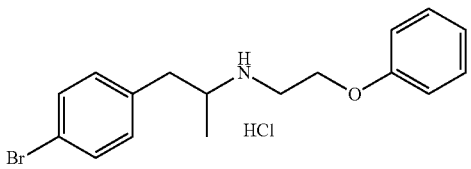 [SMILES: CC(Cc1ccc(Br)cc1)NCCOc1ccccc1 ; Cl] | 2.0 ± 0.1 | 0.0013 ± 0.009 |
| 21 | 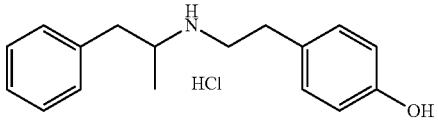 [SMILES: CC(Cc1ccccc1)NCCc1ccc(O)cc1 ; Cl] | 1.5 ± 0.2 | 0.12 ± 0.01 |
| 22 | 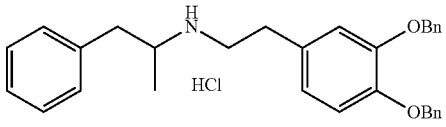 [SMILES: CC(Cc1ccccc1)NCCc1ccc(OCc2ccccc2)c(OCc2ccccc2)c1 ; Cl] | 2.0 ± 0.1 | 0.12 ± 0.001 |
| 23 | 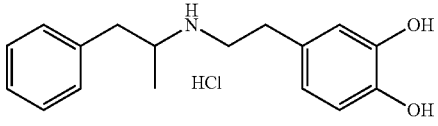 [SMILES: CC(Cc1ccccc1)NCCc1ccc(O)c(O)c1 ; Cl] | 3.4 ± 0.6 | 0.092 ± 0.017 |
| 24 | 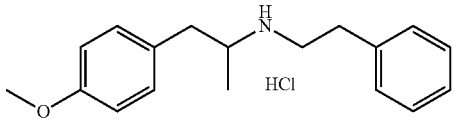 [SMILES: COc1ccc(CC(C)NCCc2ccccc2)cc1 ; Cl] | 3.77 ± 0.99 | 0.074 ± 0.002 |
| 25 | 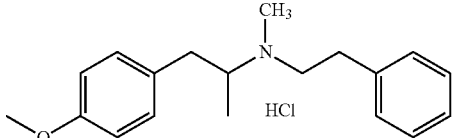 | 11.9 ± 1.84 | 0.46 ± 0.075 |
| 26 | 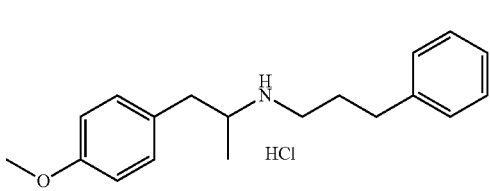 [SMILES: COc1ccc(CC(C)NCCCc2ccccc2)cc1 ; Cl] | 1.27 ± 0.09 | 0.022 ± 0.003 |

TABLE 1-continued

| Compound | Structure | [³H]DTBZ binding (Ki) VMAT2 (μM) | [³H]DA Uptake (Ki) VMAT2 (μM) |
|---|---|---|---|
| 27 | 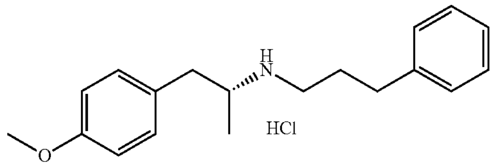 [SMILES: COc1ccc(C[C@@H](C)NCCCc2ccccc2)cc1 ; Cl] | — | 0.045 ± 0.004 |
| 28 | 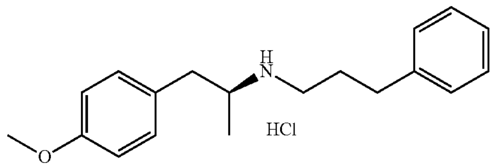 [SMILES: COc1ccc(C[C@H](C)NCCCc2ccccc2)cc1 ; Cl] | — | 0.020 ± 0.001 |
| 29 | 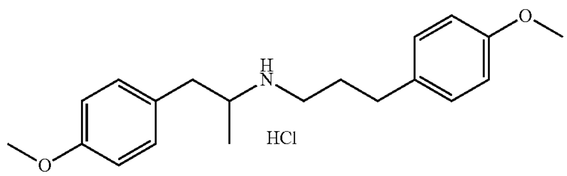 | 0.41 ± 0.14 | 0.011 ± 0.002 |
| 30 | 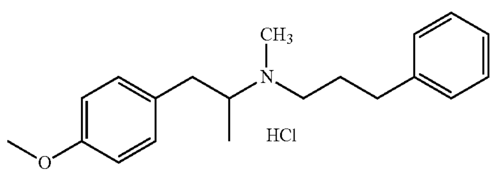 [SMILES: COc1ccc(CC(C)N(C)CCCc2ccccc2)cc1 ; Cl] | 7.11 ± 0.82 | 0.27 ± 0.038 |
| 31 | 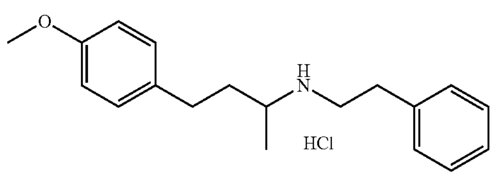 [SMILES: COc1ccc(CCC(C)NCCc2ccccc2)cc1 ; Cl] | 2.4 ± 0.1 | 0.062 ± 0.029 |
| 32 | 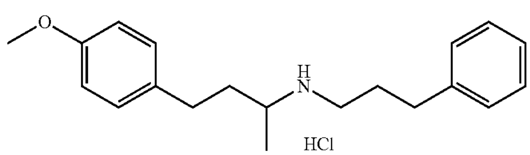 [SMILES: COc1ccc(CCC(C)NCCCc2ccccc2)cc1 ; Cl] | 4.7 ± 0.4 | 0.030 ± 0.002 |
| 33 | 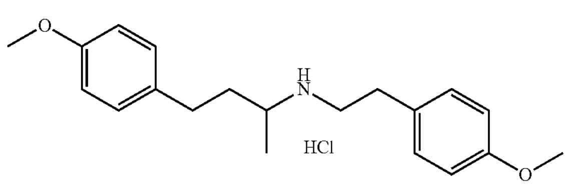 | 1.5 ± 0.2 | 0.060 ± 0.007 |
| 34 | 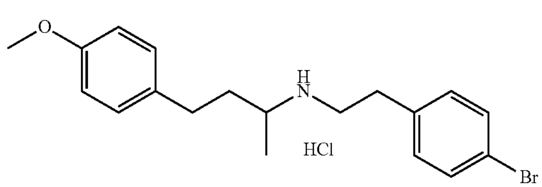 [SMILES: COc1ccc(CCC(C)NCCc2ccc(Br)cc2)cc1 ; Cl] | 0.87 ± 0.03 | 0.010 ± 0.004 |
| 35 | 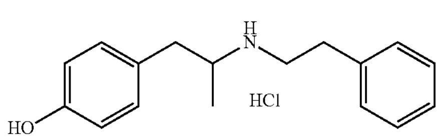 [SMILES: CC(Cc1ccc(O)cc1)NCCc1ccccc1 ; Cl] | 2.6 ± 0.4 | 0.047 ± 0.006 |

TABLE 1-continued

| Compound | Structure | [³H]DTBZ binding (Ki) VMAT2 (μM) | [³H]DA Uptake (Ki) VMAT2 (μM) |
|---|---|---|---|
| 36 | 4-HO-C6H4-CH2-CH(CH3)-NH-(CH2)3-C6H4-4-OMe · HCl | 0.23 ± 0.06 | 0.072 ± 0.030 |
| 37 | 4-HO-C6H4-CH2-CH(CH3)-NH-(CH2)3-C6H5 · HCl | 0.82 ± 0.27 | 0.033 ± 0.008 |
| 38 | 4-F-C6H4-CH2-CH(CH3)-NH-(CH2)2-C6H5 · HCl | 2.5 ± 1.6 | 0.069 ± 0.009 |
| 39 | 4-F-C6H4-CH2-CH(CH3)-NH-(CH2)3-C6H5 · HCl | 1.3 ± 0.3 | 0.010 ± 0.0002 |
| 40 | 4-F-C6H4-CH2-CH(CH3)-NH-(CH2)3-C6H4-4-OMe · HCl | 1.7 ± 0.4 | 0.017 ± 0.003 |
| 41 | 4-O2N-C6H4-CH2-CH(CH3)-NH-(CH2)2-C6H5 · HCl | 5.1 ± 1.2 | 0.060 ± 0.007 |
| 42 | 4-O2N-C6H4-CH2-CH(CH3)-NH-(CH2)3-C6H5 · HCl | 2.0 ± 0.3 | 0.013 ± 0.004 |
| 43 | 4-O2N-C6H4-CH2-CH(CH3)-NH-(CH2)3-C6H4-4-OMe · HCl | 1.4 ± 0.4 | 0.008 ± 0.002 |
| 44 | 4-H2N-C6H4-CH2-CH(CH3)-NH-(CH2)2-C6H5 · 2HCl | 17 ± 6.6 | 0.21 ± 0.08 |

TABLE 1-continued

| Compound | Structure | [³H]DTBZ binding (Ki) VMAT2 (μM) | [³H]DA Uptake (Ki) VMAT2 (μM) |
|---|---|---|---|
| 45 | 4-H₂N-C₆H₄-CH₂-CH(CH₃)-NH-(CH₂)₃-C₆H₅ · 2HCl | 2.8 ± 0.7 | 0.036 ± 0.003 |
| 46 | 3,4-(MeO)₂-C₆H₃-CH₂-CH(CH₃)-NH-(CH₂)₃-C₆H₅ · HCl | 3.8 ± 0.1 | 0.14 ± 0.013 |
| 47 | 3,4-(MeO)₂-C₆H₃-CH₂-CH(CH₃)-NH-(CH₂)₄-C₆H₅ · HCl | 1.1 ± 0.1 | 0.029 ± 0.011 |
| 48 | C₆H₅-(CH₂)₂-CH(CH₃)-NH-(CH₂)₂-C₆H₅ · HCl | 1.60 ± 0.33 | 0.050 ± 0.004 |
| 49 | C₆H₅-(CH₂)₂-CH(CH₃)-N(CH₃)-(CH₂)₂-C₆H₅ · HCl | 29.8 ± 11.2 | 0.084 ± 0.004 |
| 50 | C₆H₅-(CH₂)₂-CH(CH₃)-NH-(CH₂)₃-C₆H₅ · HCl | 4.81 ± 1.13 | 0.050 ± 0.012 |
| 51 | C₆H₅-(CH₂)₂-CH(CH₃)-N(CH₃)-(CH₂)₃-C₆H₅ · HCl | 17.2 ± 6.33 | 0.36 ± 0.034 |
| 52 | C₆H₅-(CH₂)₂-CH(CH₃)-NH-(CH₂)₃-C₆H₄-4-OMe · HCl | 3.2 ± 0.1 | 0.026 ± 0.002 |
| 53 | 4-MeO-C₆H₄-(CH₂)₂-CH(CH₃)-NH-(CH₂)₃-C₆H₄-4-OMe · HCl | 1.5 ± 0.7 | 0.024 ± 0.006 |

As illustrated by Table 1, compounds of the invention exhibited high affinity at VMAT2 as well as selectivity at VMAT2 over hERG, DAT, and SERT. For example, Compound 9 exhibited a $K_1$ value of 8.71±3.65 at VMAT2, and Compound 10 exhibited a $K_1$ value of 25.5±3.57 nM at VMAT2. Further, both Compound 9 and Compound 10 exhibited a >30-fold selectivity at VMAT2 over hERG, DAT, and SERT.

The compounds of the invention were also evaluated for their effect on METH-stimulated locomotor activity was evaluated in rats. The compounds were observed to exhibit a significant reduction of METH-stimulated locomotor activity after administration. For example, a significant reduction of METH-stimulated locomotor activity was observed after administration of Compound 9 (3 mg/kg, s.c.) and Compound 10 (17 mg/kg, s.c.).

The foregoing description and examples have been set forth merely to illustrate the invention and are not meant to be limiting. Since modifications of the described embodiments incorporating the spirit and the substance of the invention may occur to persons skilled in the art, the invention should be construed broadly to include all variations within the scope of the claims and equivalents thereof.

The invention claimed is:

1. A method of treating a substance use disorder of methamphetamine, drug dependence/abuse of methamphetamine, or withdrawal from drug dependence/abuse of methamphetamine in an individual in need thereof comprising administering a compound of formula (I), where the compound of formula (I) is (S)-3-(4-methoxyphenyl)-N-(1-phenylpropan-2-yl)propan-1-amine; (R)-3-(4-methoxyphenyl)-N-(1-phenylpropan-2-yl)propan-1-amine; or pharmaceutically acceptable salt thereof.

2. The method of claim 1, wherein the compound of formula (I) is (S)-3-(4-methoxyphenyl)-N-(1-phenylpropan-2-yl)propan-1-amine hydrochloride.

3. The method of claim 1, wherein the (S)-3-(4-methoxyphenyl)-N-(1-phenylpropan-2-yl)propan-1-amine; (R)-3-(4-methoxyphenyl)-N-(1-phenylpropan-2-yl)propan-1-amine; or pharmaceutically acceptable salt thereof is present in a pharmaceutical composition further comprising a pharmaceutically acceptable excipient.

4. The method of claim 3, wherein the pharmaceutical composition is administered to the individual by inhalation; topically; orally; intravenously as an infusion or injection; or subcutaneously as an infusion, injection, or depot formulation; transdermally; or rectally.

* * * * *